United States Patent
Kelley et al.

(10) Patent No.: US 12,214,217 B2
(45) Date of Patent: Feb. 4, 2025

(54) DEVICE AND METHOD FOR SUPPORTING TISSUE UNDERGOING RADIATION

(71) Applicants: Jill Kelley, Tampa, FL (US); Scott T. Kelley, Tampa, FL (US)

(72) Inventors: Jill Kelley, Tampa, FL (US); Scott T. Kelley, Tampa, FL (US)

( * ) Notice: Subject to any disclaimer, the term of this patent is extended or adjusted under 35 U.S.C. 154(b) by 0 days.

(21) Appl. No.: 18/607,185

(22) Filed: Mar. 15, 2024

(65) Prior Publication Data
US 2024/0307706 A1    Sep. 19, 2024

Related U.S. Application Data

(60) Provisional application No. 63/452,194, filed on Mar. 15, 2023.

(51) Int. Cl.
*A61N 5/10*     (2006.01)
*A61F 2/04*     (2013.01)

(52) U.S. Cl.
CPC .............. *A61N 5/1002* (2013.01); *A61F 2/04* (2013.01); *A61F 2002/045* (2013.01); *A61N 2005/1094* (2013.01)

(58) Field of Classification Search
CPC .................................... A61N 5/10; A61F 2/04
See application file for complete search history.

(56) References Cited

U.S. PATENT DOCUMENTS

| | | | |
|---|---|---|---|
| 8,092,472 B2 | 1/2012 | Cerier | |
| 8,663,086 B2 | 3/2014 | Duncan et al. | |
| 9,827,135 B2 | 11/2017 | Fong et al. | |
| 11,896,229 B2 | 2/2024 | Pic et al. | |
| 2007/0100420 A1 | 5/2007 | Kavanagh et al. | |
| 2009/0281634 A1 | 11/2009 | Abell et al. | |
| 2011/0098732 A1* | 4/2011 | Jacobs | A61B 17/0643 606/153 |
| 2011/0137428 A1* | 6/2011 | Terliuc | A61F 2/95 604/8 |
| 2011/0319902 A1 | 12/2011 | Epstein | |
| 2018/0078257 A1* | 3/2018 | Buttar | A61B 17/00234 |
| 2018/0353653 A1* | 12/2018 | Reid | A61P 1/18 |
| 2021/0236131 A1* | 8/2021 | Anderson | B32B 27/365 |

* cited by examiner

*Primary Examiner* — Thaddeus B Cox
*Assistant Examiner* — Joshua Daryl D Lannu

(57) ABSTRACT

The device can be used in a method to protect tissue in the gastrointestinal tract of a patient during radiation therapy, the method comprising positioning a biodegradable device to cover a perforation at a perforation site on a tissue of a patient prior to applying radiation therapy, closing the perforation through surgery, and securing the biodegradable device to cover the perforation site, so that the biodegradable device protects the tissue adjacent to the perforation site during radiation therapy. Wherein the biodegradable device is a biodegradable tubular straw or surgical patch. The surgical patch is a medical device made of tissue engineered materials designed to cover, repair, or augment damaged or weakened tissue or organs during surgery.

12 Claims, 3 Drawing Sheets

DEVICE AND METHOD FOR SUPPORTING TISSUE UNDERGOING RADIATION

RELATED APPLICATIONS

The present application claims the benefit of the filing date of U.S. Provisional Patent Application No.: 63/452,194, filed Mar. 15, 2023, the disclosures of which are hereby incorporated by reference herein in their entirety.

FIELD OF INVENTION

This application is directed to a device for insertion into body lumens to provide protection and/or support to the lumens/tissue during and/or after treatment such as radiation.

BACKGROUND OF INVENTION

The gastrointestinal (GI) tract extends from the esophagus to the anus and serves many functions, including nutrition, hydration, and disease prevention. Resection of a portion of the GI tract, such as esophagus, stomach, small intestine, large intestine or colon, is performed on a patient under general anesthesia. An incision is typically made in the abdomen, chest or neck and a diseased portion is removed. The healthy ends that remain are sewn or stapled together and the incision is closed through the procedure known as anastomosis.

Gastrointestinal doctors use colonoscopy or endoscopy procedures to treat the colon or any GI tract lumen to remove cancerous or precancerous polyps. Such procedures include polypectomy or endoscopic mucosal resection (EMR) to remove such sections of cancerous or precancerous tissue. After such procedures, radiation therapy is sometimes provided to shrink or destroy any cancer cells remaining which can proliferate and create risks to the patients. Such forms of radiation include external beam radiotherapy, unsealed source radiotherapy wherein a therapeutic is localized injected to the body, brachytherapy where a sealed radiation source is placed inside or next to the area requiring treatment, etc. In each of these radiation applications, the tissue can be weakened and thus the integrity of the tissue can deteriorate which can have adverse effects.

That is, in certain instances, radiation in attempting to shrink the tumor, damages healthy surrounding tissue which can weaken the body lumen. This is especially the case since the radiation therapy is applied over a period of time, either intermittently or continuously. In some cases, the weakened tissue can result in leakage of the body lumen or a perforation. Leakage and/or perforation may lead to adverse effects such as contamination of the peritoneal or thoracic cavity, sepsis, morbidity, and even death. The radiation can also weaken the anastomotic site.

A perforation results from injury to the mucosa of the bowel wall resulting from a violation of the closed system. This can be from an ulceration or trauma or iatrogenic cause (instrumentation). Bowel perforation can be secondary to many factors, most commonly inflammation, infection, obstruction, trauma, or invasive procedure. Diverticulitis is an example of a perforation. Anastomotic leakage is another. This exposes the structures within the peritoneal cavity to gastrointestinal contents. Such occurrences can be life-threatening due to the risk of developing infections such as peritonitis. Surgery is often necessary to close the perforation and/or divert the enteric contents away from the area of the perforation via, for example, a colostomy.

It would be advantageous to provide a device for use with surgical procedures for early colon or other GI tract cancers removed by colonoscopy and also early cancers removed via endoscopy requiring post-surgery radiation which would protect the tissue undergoing radiation, i.e., prevent or at least limit, the effect of tissue damage during radiation.

Advances in minimally invasive procedures allow entry into body lumens without major surgery. It would be advantageous to provide such device to protect tissue undergoing radiation which could be inserted via such a minimally invasive procedure.

SUMMARY OF THE INVENTION

Commonly owned U.S. Pat. No. 8,894,699 (hereinafter the '699 patent) discloses devices which effectively addressed reducing the risk of leaks at the anastomotic site. The devices disclosed are in the form of a covered stent providing a scaffold. An impermeable layer is placed over and attached to the scaffold. The device is inserted between or into the lumen ends to be anastomosed to provide stability and/or structure to the anastomosed lumen.

The inventor of the '699 patent, along with the inventor of the present application, conceived of modifications to the device of the '699 patent which could provide advantages in certain clinical applications, as well as conceived of new advantageous uses of the devices to support tissue during cancer treatment, such as during radiation, as well as provide support after radiation therapy.

The disclosed device can protect the tissue at an anastomotic site and may provide a shield from harmful gamma rays during cancer treatment. The device can be placed minimally invasively during surgery and may provide anastomotic protection from the harmful effects of radiation, such as during brachytherapy procedures.

In one aspect, the present invention provides a protective device in the form of a biodegradable tubular structure to provide a support for the body lumen which could be damaged during radiation. An adhesive can be utilized to attach the tubular structure to the body lumen and the adhesive can also provide a sealant. The device can be placed prior to the radiation treatment, and does not interfere with the treatment. The device can be left in place after the radiation to provide support during intervals between radiation, and can be left in after the radiation treatment/therapy is complete. The device is inserted minimally invasively and because of it being biodegradable, it does not require another procedure for removal. It degrades as healthy tissue growth is restored.

The tubular device of the present disclosure is in the form of a straw with a thin wall and a lumen extending therethrough and has open proximal and distal ends to enable flow therethrough. The tubular device in some embodiments may incorporate a rim or rib at a top portion of the device or can be a colon- shaped device. ("Top" referring to the portion/region closer to the head of the patient).

In another aspect of the present disclosure, the tubular device can be made of tissue engineered material (e.g., from tissue generated organs), and may be placed in the colon to provide extra support to seal an anastomosis or weakened tissue. In some embodiments, the tissue generated material comprises colon cells.

In another aspect of the present disclosure, the tubular device may be biodegradable.

In accordance with another aspect of the present disclosure, a method to support a body lumen during radiation treatment is provided comprising the steps of a) positioning a tubular straw like device in a body lumen of the gastrointestinal tract prior to treatment; b) securing the device to the intestine utilizing an adhesive; and c) leaving the device in place after the radiation treatment to enable it to degrade.

The device in some embodiments can also include a treatment or healing substance, e.g., a drug, adhered thereto.

In accordance with another aspect of the present disclosure, a method to add integrity to a tissue site undergoing radiation is provided comprising the steps of a) positioning a tubular straw like device in a lumen of the body region; and b) securing the device to the lumen utilizing an adhesive, the device providing support for the tissue region weakened by the radiation.

The foregoing methods utilize in some embodiments, a tubular device having an enlarged rim providing a diameter larger than other regions of the device. The rim is at the top portion of the device and in some embodiments provides a radial force against the tissue (e.g., colon wall), to help secure the device in place. The device can be held in place by an adhesive. In preferred embodiments, the adhesive utilized has a dual function: adhering the device to the tissue (e.g., luminal wall), and providing a seal to prevent unwanted flow.

In some embodiments, the device is further secured by one or more sutures.

In accordance with another aspect of the present invention the device is composed of a tissue engineered material and held in place at the rim by an adhesive.

BRIEF DESCRIPTION OF THE DRAWINGS

So that those having ordinary skill in the art to which the subject invention appertains will more readily understand how to make and use the apparatus (device) disclosed herein, preferred embodiments thereof will be described in detail hereinbelow with reference to the drawings, wherein:

FIGS. 5 and 6 are perspective views of an alternate embodiment of the device of the present disclosure placed over the first and second gastrointestinal tract portions, wherein:

FIG. 5 shows the tubular device inserted over the first gastrointestinal tract portion, the second gastrointestinal tract portion not yet attached; and FIG. 6 shows the tubular device positioned over the first and second gastrointestinal tract portions, the second gastrointestinal tract portion being placed in apposition (abutment) with the first gastrointestinal tract portion;

DETAILED DESCRIPTION OF THE DRAWINGS

Figure 1:
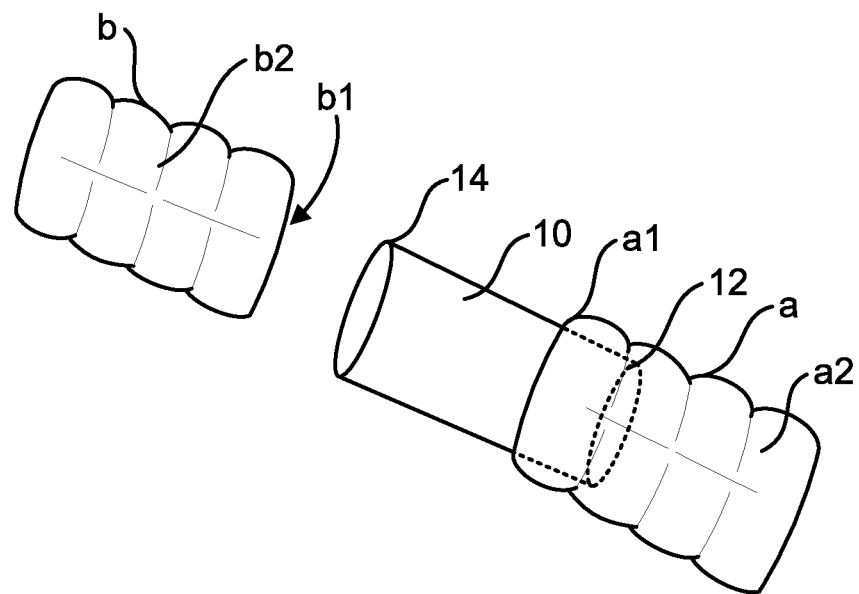
FIG. 1 is a perspective view of an embodiment of the tubular device of the present invention shown inserted into a lumen of a first gastrointestinal tract portion (section), a second intestine portion (section) not yet attached.

As noted above, commonly owned U.S. Pat. No. 8,894,699, incorporated herein by reference in its entirety, and having a common inventor with the present application, disclosed devices which effectively addressed leakage at the anastomotic site. The devices disclosed are in the form of a covered stent providing a scaffold inserted between or into the lumen ends to be anastomosed to provide stability and/or structure to the anastomosed lumen.

The inventor of the '699 patent, along with the other inventor of the present application, conceived of modifications to the device which could provide advantages in certain clinical applications, as well as conceived of new advantageous uses of the device, which are described in detail below.

The device disclosed in the present application provides a tubular structure, also referred to herein as a straw-like structure. The tubular straw-like structure is impermeable and preferably composed of a biodegradable material which will degrade within the body after a period of time. The tubular structure in some embodiments provides structure and/or stability to the body lumens which can thereby protect the tissue undergoing radiation therapy. The tubular structure has a thin wall and a lumen extending therethrough, and has an open top and bottom end. "Top" and "bottom" as used herein refer to orientation wherein top is closer to the patient's head and bottom is further from the patient's head. Also, "top" and "bottom" as used herein relates to direction of flow of body fluids or substances (e.g., the stool passes from the top to bottom). "Proximal" as used herein can also refer to the top portion and "distal" as used herein may refer to the bottom portion, also relating to flow/passage.

The tubular structure can be formed of one piece which provides the advantages of ease of manufacture and more flexibility as opposed to the use of covered stents which need to have an impermeable cover attached to the inner structure (e.g., a frame).

The device can be used in a method to protect tissue in the gastrointestinal tract of a patient during radiation therapy, the method comprising positioning a biodegradable device to cover a perforation at a perforation site on a tissue of a patient prior to applying radiation therapy, closing the perforation through surgery, and securing the biodegradable device to cover the perforation site, so that the biodegradable device protects the tissue adjacent to the perforation site during radiation therapy. Wherein the biodegradable device is a biodegradable tubular straw or surgical patch. The surgical patch is a medical device made of tissue engineered materials designed to cover, repair, or augment damaged or weakened tissue or organs during surgery.

In some embodiments, the tubular device of the present invention is used with an anastomosis of two body lumens, such as two portions of the f, where radiation is applied after the anastomosis to shrink or destroy any remaining cancerous microcells remaining after resection of the gastrointestinal tract portion. In other embodiments, the tubular device is used in an area where a polyp or cancerous tumor has been removed from the body lumen and the surrounding tissue is subject to radiation therapy to shrink or destroy any remaining cancerous microcells remaining after polyp or tumor removal. Various other clinical applications of the tubular straw-like device of the present disclosure are also contemplated.

For example, gastrointestinal doctors use colonoscopy or endoscopy procedures to treat the colon or any GI tract lumen to remove cancerous or precancerous polyps. Such procedures include polypectomy or endoscopic mucosal resection (EMR) to remove such sections of cancerous or precancerous tissue. After such procedures, radiation therapy is also provided to shrink or destroy any cancer cells remaining which can proliferate and create risks to the patients. Such forms of radiation include external beam radiotherapy, unsealed source radiotherapy wherein a therapeutic is localized injected to the body, brachytherapy where a sealed radiation source is placed inside or next to the area requiring treatment, etc. In each of these radiation applications, the tissue can be weakened and thus the integrity of the tissue can deteriorate which can have adverse effects. The device of the present disclosure protects the tissue from harmful effect of radiation (e.g., to shield the tissue from harmful gamma rays).

Thus, the device of the present disclosure can function to a) shield the tissue from harmful rays of radiation therapy; and b) maintain the structural integrity of the body lumen which would otherwise be weakened by the radiation therapy.

Figure 2:
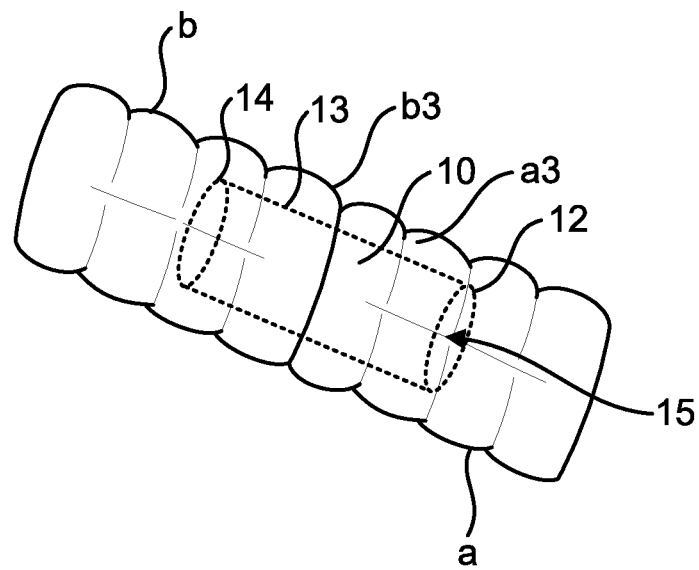
FIG. 2 is a perspective view similar to FIG. 1 showing the tubular device inserted into the lumen of the second gastrointestinal tract portion, the second gastrointestinal tract portion placed in apposition (abutment) with the first gastrointestinal tract portion.

Referring now to the drawings and particular embodiments of the present disclosure, wherein like reference numerals identify similar structural features of the devices throughout the several views, the device (stent) of a first embodiment of the present invention is designated generally by reference numeral 10. Device 10 is in the form of a biodegradable straw and has a proximal/top open end 12 and an opposite distal/bottom open end 14. Device 10 can have various dimensions. Proximal end 12 is dimensioned (i.e., outer dimension), to be inserted into opening a1 and into lumen a2 of first gastrointestinal tract portion a, and distal end 14 is dimensioned (i.e., outer dimension), to be inserted into opening b1 and into lumen b2 of second gastrointestinal tract portion b. Thus, the inner dimension of gastrointestinal tract lumen a2, b2 may be greater than the outer dimension of device 10. FIG. 1 illustrates proximal end 12 of device 10 inserted into lumen portion a2 and not yet inserted into lumen portion b2. FIG. 2 illustrates device 10 inserted into both lumen portions a2, b2 and the openings a1, b1 approximated and in contact (abutment) for anastomosis. The inner diameter of device lumen 15 is dimensioned to accommodate body fluid flow and maintain unobstructed passage through the gastrointestinal tract. Note the drawings of FIGS. 1-9 do not illustrate the inner diameter of lumens a2, b2, and therefore appear to show a large space between the inner wall of lumen portions a2, b2 and the outer surface of device 10. In application however, the outer dimension of device 10 may be close to the inner dimension of gastrointestinal tract lumen a2 and/or b2 as explained below.

In practice, lumen portions a2, b2 and gastrointestinal tract portions a, b, may be separated, and a diseased (e.g., cancerous), portion may be removed (not shown). After removal, the surgeon may insert first end 12 of tubular device 10 into first lumen end a1 of the separated lumen portion a2 (or the separated lumen a2 is placed over end 12 of device 10). The second end 14 of the tubular device 10 may then be inserted into second lumen b2 (or second lumen end b2 may be placed over end 14 of device 10), and lumens a2, b2 and gastrointestinal tract portions a, b are attached to each other by various methods such as suturing, stapling and/or use of an adhesive to create an anastomotic site.

Tubular device 10 can in some embodiments be inserted into gastrointestinal tract a, b prior to anastomosis to act not only as a tissue shield during radiation but as a prophylactic measure against leakage and/or soilage to prevent further inconvenience and potential complications associated with treating compromised or weakened lumens a2, b2. Additionally, the use of device 10 may prevent scarring at lumen ends a1, b1 and may eliminate or reduce constrictions (strictures) caused by closure of the lumen, such as by scarring or fusion.

In some embodiments, use of device 10 may promote healing in the affected area a1, b1 of lumen a2, b2.

Apparatus and methods of the present disclosure can be utilized for anastomosis after removal of cancerous tissue/body portions in various lumens of the body. Other lumens include for example lumens located in the gastrointestinal tract, the urinary tract, the cardiovascular system, the biliary tract, pancreatic duct and the genitourinary tract. Suitable anastomosis sites may include for example the intestines, esophagus, stomach, bile ducts, pancreas, pancreatic duct, ureter, pancreas and urethra. Other body lumens/tubular structures and sites are also contemplated. Uses of device 10 other than for anastomosis are also contemplated.

In one embodiment, resection of a portion of the GI tract such as the esophagus, stomach, colon, small intestine or large intestine may be performed on a patient under general anesthesia to remove troublesome portions of luminal tissue, such as cancerous tissue. After resection, the separated lumen ends may be anastomosed, with the device 10 positioned in the luminal tissue. The device 10 is in place for radiation therapy at the anastomotic site.

Device 10 (as well as devices 20 and 30 discussed below) is shown symmetrically shaped, but asymmetrical shapes such as the ends 12, 14 being of different dimensions or configurations are also contemplated, as are shapes other than the cylindrical shape shown (e.g., funnel shaped, non-circular cross-section, etc.) Additionally, device 10 may be configured for custom sizing and/or shaping to conform to the contours of the lumen a2, b2.

In one embodiment device 10 is may be non-expandable such that its transverse dimension is the same during insertion and following placement. However, in alternate embodiments, device 10 may be collapsible/expandable such that it is inserted in a reduced diameter configuration and expanded to a larger diameter placement configuration. Expansion can be for example by an inflatable balloon or by a phase change such as with shape shape-memory polymeric materials.

The device 10 can be configured to be of a size (or expandable to a size in embodiments where the device expands) to make contact with the surrounding luminal tissue (i.e., the internal wall of the lumen), for attachment and/or support. For example, where adhesive is applied to at least part of the external surface of the device and/or at least part of the internal surface of the luminal tissue (not shown), a balloon may provide a mechanism for holding the device 10 in place while the adhesive sets.

The device 10 comprises a biocompatible, biodegradable and/or bioabsorbable material. Once in place, it may disintegrate/degrade/resorb over time (once the lumens attach), and either become absorbed into or pass through the body so invasive mechanical removal is not necessary.

The tubular structure preferably provides a continuous outer wall (without openings) to provide a sealed structure along its length.

In some embodiments, the device can be composed of tissue engineered material. For example, the device can me made of cells of an organ such as colon cells.

Figure 8:
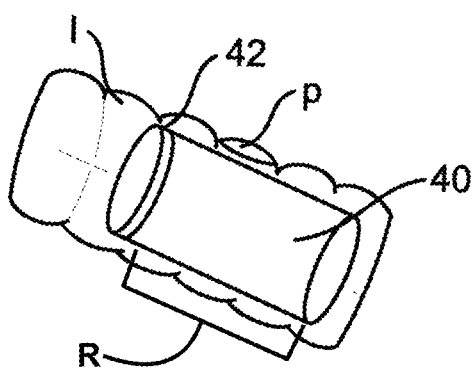
FIG. 8 is a perspective view showing the tubular device inserted into a body lumen to protect the tissue at a site where a polyp has been removed and radiation therapy is being applied.
Figure 9:
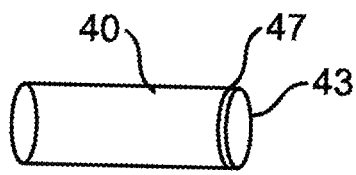
FIG. 9 is a perspective view of an alternate embodiment of the tubular device having a thickened rim portion.

In some embodiments, the device can be formed in a configuration having with a rim (rib top) to provide a holding force to hold the device 10 against the tissue/organ (e.g., colon), as shown in FIG. 8. The rim 42 of device 40 can create a radial force against the body lumen (e.g., colon), to help hold it in place. Rim 42 being at the top (i.e., closer to the head), and may provide a seal to prevent passage of stool or other luminal fluid between device 10 and an outer surface of device 10. An adhesive can be placed on the tip of rim 42 of the device to help hold it in place and provide a seal. The top of device 10 can, in some embodiments be thicker to provide additional support as shown for example in FIG. 8. Thus, the device of FIGS. 8 and 9 serve two functions: securement in place of device 10 within lumen 1, and sealing the body lumen from unwanted passage proximal to rim 42, 47. In one embodiment, the adhesive 43 need only be applied to the rim portion 42, 47 (top), although it is also envisioned that adhesive 43 may be applied to other regions of the device.

The adhesive 43 can be applied around the periphery (circumference) of device 40. The adhesive 43 around the rim 42, 47 periphery can provide the sole adhesive, or alternatively adhesive 43 could be provided on other regions of device 40.

The device 10 can include an adhesive applied thereon during the surgical procedure. The adhesive can be applied to a portion or to the entire external surface during the surgery and then the device inserted into intestinal portions as shown in FIG. 2 wherein the adhesive surface comes into contact with the inner wall of the lumen to adhesively attach the device 10 within the lumen. Note the drawings show the device not in contact with the inner wall of the lumen for clarity, it being understood, that during use the device can be configured to be of a size such that at least portions of the outer wall of the device are in contact/abutment with the inner wall of the lumen so the adhesive is pressed between the outer wall 13 of device 10 and the inner wall a3, b3 of the lumens of intestine portions a, b.

Figure 3:
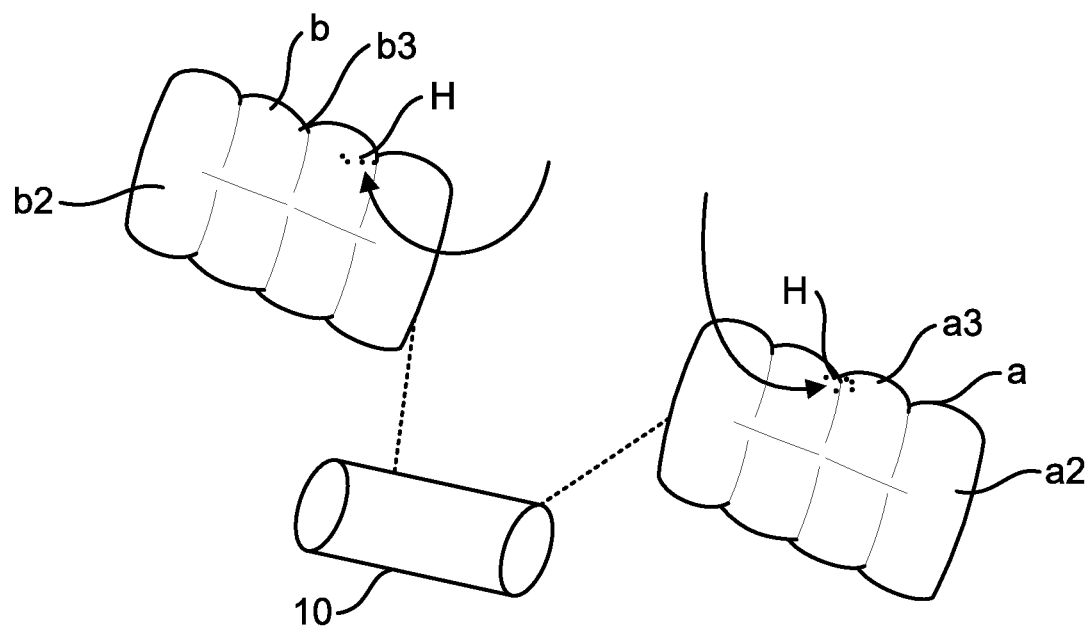
FIG. 3 illustrates an alternate embodiment wherein the adhesive is applied to the internal wall of the lumens of the first and second gastrointestinal tract portions prior to insertion of the tubular device of FIG. 1.
Figure 4:
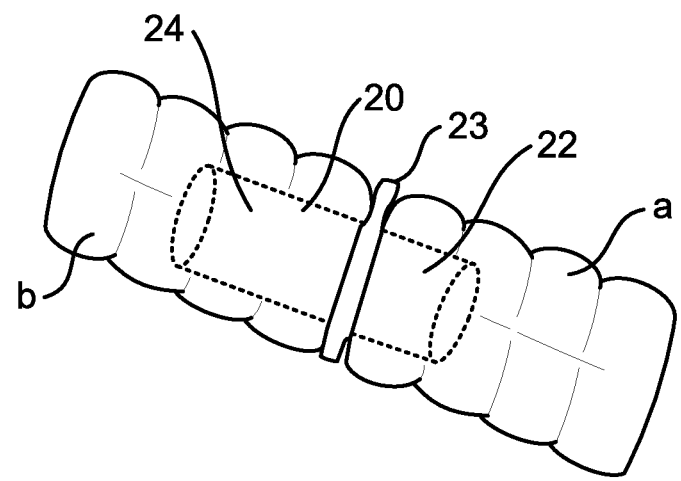
FIG. 4 is a perspective view of an alternate embodiment of the tubular device of the present invention having an enlarged region to bridge the gap between the first and second gastrointestinal tract portions which are not in abutment.

In the alternate embodiment of FIG. 3, the adhesive H is applied solely to the inner wall a3, b3 of intestine portions a, b as shown schematically by the arrows. The device 10, without any adhesive applied thereto, would then be inserted into the lumens a2, b2 after such application of adhesive to adhere to the inner walls a3, b3.

The adhesive, in alternate embodiments, could be applied to device 10 prior to the surgery rather than during the surgery and activated during the procedure. That is, the adhesive could be applied to the external wall of the device 10 prior to the surgical procedure and then activated, e.g., via warming by body temperature, or by another device, to release the adhesive to provide adherence of the device 10 to the lumen walls a3, b3.

In the embodiment of FIG. 2, the device 10 is inserted into the lumens of the two separated gastrointestinal tract portions a, b, and the two portions/lumens are brought into contact/abutment for the anastomosis. In the alternate embodiment of FIG. 4, device 20 has an enlarged diameter region 23 between ends 22 and 24 at a midway portion between the two ends of device 20 or alternatively closer to one of the ends. The enlarged region 23 bridges the gap between intestinal portions a, b (i.e., the portions a, b are in abutment with the enlarged region 23), on opposing sides. In some embodiments, the enlarged region 23 can have an outer diameter substantially equal to the outer diameter of portions a, b, although other outer diameters are also contemplated. In the embodiment illustrated in FIG. 4, adhesive could also be applied to enlarged region 23 and/or sections a, b where they abut. The ends 22 and 24 are within the lumens of portions a, b and thus have a smaller outer diameter than the inner diameter of portions a, b. Device 20 can be made of the same material, can be of various symmetrical and asymmetrical forms, and function to provide structure in the same manner as device 10.

Figure 5:
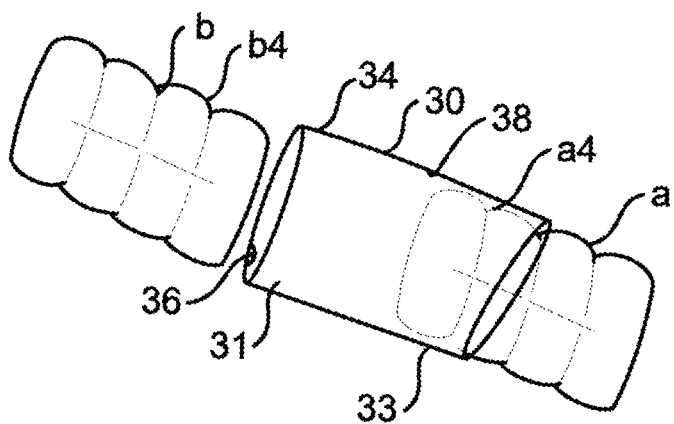
Figure 6:
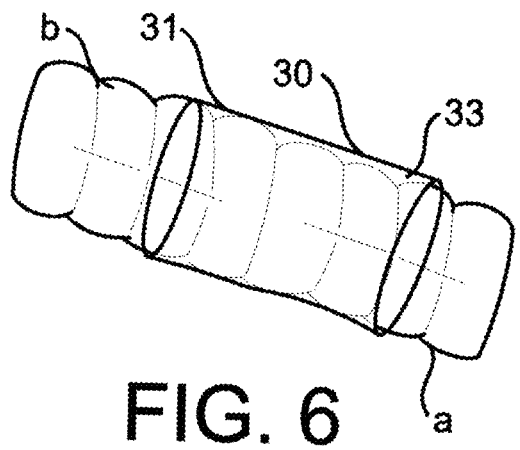
Figure 7:
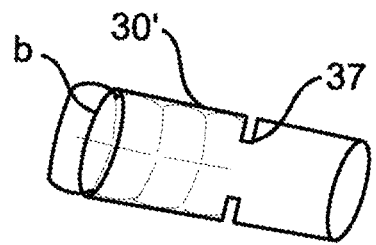
FIG. 7 is a perspective view of an alternate embodiment of the tubular device having an inward extension.

In the alternate embodiment of FIGS. 5 and 6, device 10 is dimensioned so that it is placed over the external wall of the intestine sections a, b rather than inside the lumen of portions (sections) a, b as in FIG. 1. More specifically, device 30 has a first end 33 and a second opposite end 34 and a wall 38. The device 30 is shown in FIG. 5 placed over the outer wall a4 of intestine portion a. Intestine portion b is then received into lumen 31 of device 30 through opening 36 such that wall 38 is positioned over outer wall b4 of intestine section b. FIG. 6 illustrates the device 30 placed over both intestine sections a, b, and the sections a, b in abutment for anastomosis. As can be appreciated, in this embodiment, the inner diameter of device 30 would be greater than the outer diameter of the intestine portions a, b to accommodate the portions a, b, within its lumen 31. The device 30 could alternatively include an inwardly extending portion for positioning between the two portions a, b such that the portions a, b abut the inward extension rather than each other for anastomosis (see extension 37 of device 30' of FIG. 7).

Adhesive can be applied to the outer wall of the intestine sections a, b for attachment to the device 30. Alternatively, an adhesive can be applied to the inner wall of device 30 in lieu of adhesive application to the outer wall of sections a, b or in addition to adhesive application to the outer wall of sections a, b. Device 30 (and device 30') can be made of the same material, can be of various symmetrical and asymmetrical forms, and function to provide structure in the same manner as device 10.

In another embodiment, the devices of the present invention can include a composition to promote healing, such as a growth factor, antimicrobial agent, antibody and/or the like. Growth factors comprise cellular proteins that assist in cellular proliferation and differentiation. Antimicrobial agents, including antivirals, antibiotics and antifungals, prevent harmful bacteria, viruses and/or other microbes from infecting the anastomosed site and interfering with the tissue healing and growth processes. Certain types of antibodies may be implemented to bind with foreign objects, such as bacteria and viruses that would be harmful to the healing site if not contained, e.g., preventing strains of bacteria causing leaks. Chemotherapeutic agents can be included on the device to diffuse into the tissue site. Thus, the device in addition to protecting tissue, can serve other healing and/or treatment functions, and its biodegradable aspect avoids having to remove the device after healing or treatment.

Various uses of the devices are contemplated herein. Some examples are provided below, it being understood the devices of the present invention disclosed herein can be used in clinical applications and in other parts/regions of the body in addition to those specifically disclosed herein. FIG. 8 illustrates the device 40 of FIG. 9, having an enlarged rim 42, positioned in the intestine at the site R adjacent the area of removal of a polyp. The device 40 protects the body lumen during radiation treatment at the site R.

In another application, the device be used in an area to be radiated to limit tissue damage. Thus, it can add integrity to the tissue site. This may enable radiation to start sooner since the device provides a support for previously weakened tissue.

Adhesives according to various aspects of the present invention may comprise any suitable material to attach, adhere and/or bond to living tissue. Adhesives may comprise natural, naturally derived and/or synthetic materials. The adhesive may comprise a gel, liquid and/or solid. Examples of adhesives that can be used include purified bovine serum albumin and glutaraldehyde, (sold commercially as Bioglue & by Cryolife Technology, Inc., Kennesaw Georgia). The adhesive can comprise polyethylene glycol, sold commercially as Duraseal R Sealant by Confluent Surgical, Inc., Waltham, Massachusetts pr Tiseel fibrin sealant. The adhesive applied could also be Puragel or Puracif.

In preferred embodiments, the adhesive utilized not only performs an adherence function but also forms a sealing function. Sealant surgical glue is one possible material that can be used.

Suitable methods of application of the adhesive may include spraying, topical application and/or injection. In one embodiment, a more viscous adhesive, such as Duraseal & Sealant, may be applied to decrease the setting time, thereby decreasing the time required for a surgeon to hold the ends of lumen together or the ends of a lumen against the device (scaffold). The adhesive may provide both a mechanism for attachment of lumen ends to each other after anastomosis, as well as a sealant. As described above, the adhesive may bond the device to the lumen ends and may seal the connection between the device and lumen ends. In yet another embodiment, the adhesive may be applied over the device and the lumen ends to both bond the lumen ends to the device, as well as provide a seal.

In one embodiment, once a biocompatible, biodegradable and/or bioabsorbable adhesive is in place it may be configured to disintegrate, degrade and either become absorbed into or pass through the body. For example, in an application where the lumen ends are configured to heal and reseal themselves, the adhesive may no longer be necessary to bond and/or seal the lumen, and it may desirable for the adhesive to be removed.

In alternate embodiments, a suture can be used in addition to or in lieu of the adhesive to help secure the device in place. The suture can be for example in the form a "T" that hooks in place. It can be placed in various regions of the device such as at the rim in devices like those of FIG. 9 having a rim.

The device of the present invention can be used in various methods. In one method to protect an intestine during radiation, the method includes a) positioning a tubular straw like device in a lumen of a first intestinal portion to be attached to a second intestinal portion at an anastomotic site, the tubular straw having a rim with an enlarged diameter; and b) securing the device to the intestine utilizing an adhesive, the rim blocking stool passage past the rim. In another method, a method to keep a lumen of an intestine open includes a) positioning a tubular straw like device across a narrowing in a lumen of the intestine; and b) securing the device to the intestine utilizing an adhesive, the device including a healing or treatment substance attached thereto. In another method, a method to support a tissue region during treatment such as radiation includes a) positioning a tubular straw like device across a region of the body blocked by a tumor; and b) securing the device to the intestine utilizing an adhesive top support the tissue during radiation, the device including a chemotherapeutic agent adhered thereto to shrink the tumor. In another method, a method to add integrity to a tissue site undergoing radiation includes a) positioning a tubular straw like device in a lumen of the body region; and b) securing the device to the intestine utilizing an adhesive, the device providing support for the tissue region weakened by the radiation.

Although the apparatus and methods of the subject invention have been described with respect to preferred embodiments, those skilled in the art will readily appreciate that changes and modifications may be made thereto without departing from the spirit and scope of the present invention as defined by the appended claims. Persons skilled in the art will understand that the various embodiments of the disclosure described herein and shown in the accompanying figures constitute non-limiting examples, and that additional components and features may be added to any of the embodiments discussed herein without departing from the scope of the present disclosure.

It will be understood by those skilled in the art that the above particular embodiments are shown and described by way of illustration only. The principles and the features of the present disclosure may be employed in various and numerous embodiments thereof without departing from the scope and spirit of the disclosure. The above-described embodiments do not restrict the scope of the disclosure.

Additionally, persons skilled in the art will understand that the elements and features shown or described in connection with one embodiment may be combined with those of another embodiment without departing from the scope of the present invention and will appreciate further features and advantages of the presently disclosed subject matter based on the description provided.

Throughout the present disclosure, terms such as "approximately," "about", "generally," "substantially," and the like should be understood to allow for variations in any numerical range or concept with which they are associated. It is intended that the use of terms such as "approximately", "about", "substantially", and "generally" should be understood to encompass variations on the order of 25%, or to allow for manufacturing tolerances and/or deviations in design. For example, the term "generally parallel" should be understood as referring to configurations in which the pertinent components are oriented so as to define an angle there between that is equal to 180°+25% (e.g., an angle that lies within the range of (approximately) 1350 to (approximately) 225°.

The recitation of numerical ranges by endpoints includes all numbers within the range.

Although terms such as "first," "second," "third," etc., may be used herein to describe various operations, elements, components, regions, and/or sections, these operations, elements, components, regions, and/or sections should not be limited by the use of these terms in that these terms are used to distinguish one operation, element, component, region, or section from another. Thus, unless expressly stated otherwise, a first operation, element, component, region, or section could be termed a second operation, element, component, region, or section without departing from the scope of the present invention.

Each and every claim is incorporated as further disclosure into the specification and represents embodiments of the present disclosure. Also, the phrases "at least one of A, B, and C" and "A and/or B and/or C" should each be interpreted to include only A, only B, only C, or any combination of A, B, and C.

What is claimed is:

1. A method to protect tissue in a patient's gastrointestinal tract during radiation therapy, the method comprising:

implanting an impermeable biodegradable device within a lumen of a first gastrointestinal tract portion, the impermeable biodegradable device formed as a single piece and comprising a continuous outer surface, a continuous tubular inner surface, a proximal end opening, and a second distal end opening, the proximal end opening extending into the lumen of the first gastrointestinal tract portion;

attaching a lumen of a second gastrointestinal tract portion to the lumen of the first gastrointestinal tract portion to form an anastomotic site, the distal end opening extending into the lumen of the second intestine gastrointestinal tract portion; and securing the impermeable biodegradable device to the lumen of the first gastrointestinal tract portion utilizing an adhesive applied to an external portion of the impermeable biodegradable device such that the outer surface of the impermeable biodegradable device extends across the anastomotic site, the impermeable biodegradable device protecting tissue adjacent to the anastomotic site during radiation therapy.

2. The method of claim 1, wherein the continuous outer surface of the impermeable biodegradable device has a first diameter and further comprises a rim having a second diameter larger than the first diameter, and wherein the adhesive is applied to the rim.

3. The method of claim 2, wherein the rim provides a radial force against the lumen of at least one of the first or second gastrointestinal tract portions.

4. The method of claim 1, wherein the impermeable biodegradable device is a biodegradable patch.

5. The method of claim 1, wherein the impermeable biodegradable device is a biodegradable tubular straw.

6. The method of claim 1, wherein the impermeable biodegradable device is formed of tissue engineered material.

7. The method of claim 6, wherein the tissue engineered material comprises colon cells.

8. An impermeable biodegradable device to protect gastrointestinal tract tissue of a patient during radiation therapy, the impermeable biodegradable device being formed as a single piece comprising:

an elongate tubular structure having a proximal portion,
a distal portion, and
a lumen extending from the proximal portion to the distal portion, the impermeable biodegradable device configured to be implanted into a lumen of a first gastrointestinal tract portion, the proximal portion comprising a rim, the rim having a diameter greater than other regions of the device, wherein an adhesive applied to an outer surface of the rim holds the impermeable biodegradable device in place within the gastrointestinal tract, the impermeable biodegradable device being composed of a tissue engineered material.

9. The device of claim 8, wherein the tissue engineered material comprises colon cells.

10. The device of claim 8, wherein the rim is configured to receive the adhesive for attachment of the rim to the lumen and to provide a sealant.

11. The device of claim 8, wherein the device is asymmetrical.

12. The device of claim 8, where the elongate tubular structure is used to open up blockages or obstructions.

* * * * *